United States Patent [19]

Chan et al.

[11] Patent Number: 4,721,675
[45] Date of Patent: Jan. 26, 1988

[54] PRODUCTION OF HEPATITIS A VIRUS IN VITRO UTILIZING A PERSISTENTLY VIRUS INFECTED CELL CULTURE SYSTEM

[75] Inventors: Emerson W. Chan, Bolingbrook; Joel R. Mitchen, Winthrop Harbor, both of Ill.

[73] Assignee: Abbott Laboratories, North Chicago, Ill.

[21] Appl. No.: 697,703

[22] Filed: Feb. 4, 1985

Related U.S. Application Data

[63] Continuation of Ser. No. 344,683, Feb. 1, 1982, abandoned.

[51] Int. Cl.[4] .............. C12N 7/02; C12N 7/00; C12N 5/00; A61K 39/29
[52] U.S. Cl. .............. 435/239; 435/235; 435/948; 435/240.21; 424/89
[58] Field of Search ......... 435/240, 241, 948, 237, 435/238, 239, 236, 259; 424/89

[56] References Cited

U.S. PATENT DOCUMENTS

| | | | |
|---|---|---|---|
| 4,102,996 | 7/1978 | McAleer et al. | 435/239 |
| 4,164,565 | 8/1979 | Prince et al. | 424/89 |
| 4,164,566 | 8/1979 | Provost et al. | 424/89 |
| 4,344,935 | 8/1982 | Leclerc et al. | 424/89 |
| 4,393,133 | 7/1983 | Knowles et al. | 435/948 |
| 4,412,002 | 10/1983 | McAleer et al. | 435/240 |

OTHER PUBLICATIONS

Siegl et al, "The Physiochemical Properties of Infectious Hepatitis A Virons" Journal of General Virology 37 (1981) pp. 331–341.
Gauss-Muller et al., "Propagation of Hepatitis A Virus in Human Fibroblasts" Journal of Medical Virology 7(3) (1981) pp. 233–239.
Kojima et al. "Propagation of Human Hepatitis A Virus in Conventional Cell Lines" Journal of Medical Virology 7(4) pp. 273–286 (1981) Abstract only.
Flehmig, "Hepatitis A Virus in Cell Culture. II. Growth Characteristics of Hepatitis A Virus in Frhk-4/R Cells" Medical Microbiology and Immunology 170(2) (1981) pp. 73–81.
Aden et al, "Controlled Synthesis of HBsAg in a Differentiated Human Liver Carcinoma-Derived Cell Line" Nature 282 (12-1979) pp. 615–616.
Frosner et al, "Propagation of Human Hepatitis A Virus in a Hepatoma Cell Line" Abstracts of the Annual Meeting ASM (5-1980) abstract #S 57.
Siegl et al, "Propagation of Human Hepatitis A Virus in Hepatoma Cell Cultures" Experientia 30 (1980) p. 1448.
Frosner et al, "Propagation of Human Hepatitis A Virus in a Hepatoma Cell Line" Workshop of the Virology Section of the DGHM, Zentralblatt Fhur Bakteriologie, Parasitenkunde, Infekitionskrankheiten Und Hygiene. vol. 248(1) (1980) pp. 15–16.

*Primary Examiner*—John E. Tarcza
*Attorney, Agent, or Firm*—Martin L. Katz

[57] ABSTRACT

The present invention relates to a method for producing human hepatitis A virus in vitro employing tissue culture techniques. In particular, the present invention relates to an in vitro tissue culture procedure utilizing a persistently infected cell line that produces high titers of hepatitis A virus. The hepatitis A virus thus produced is a source of hepatitis A virus antigens.

19 Claims, No Drawings

PRODUCTION OF HEPATITIS A VIRUS IN VITRO UTILIZING A PERSISTENTLY VIRUS INFECTED CELL CULTURE SYSTEM

This application is a continuation of application Ser. No. 344,683, filed 2/1/82 now abandoned.

BACKGROUND OF THE INVENTION

Various tissue culture procedures for propagating hepatitis A virus have been disclosed, such as, for example, U.S. Pat. No. 4,164,566; European Patent Application No. 25,745; Frösner, et al, Propagation of Human Hepatitis A virus in a Hepatoma Cell Line, *Infection*, 6: 303–306; Flehmig, Hepatitis A-virus in cell culture: I. Propagation of Different Hepatitis Virus Isolates in a Fetal Rhesus Monkey Kidney Cell Line (Rfnk-4), *Med. Microbiol. Immunol.*, 168: 239–248; and Daemer, et al, Propagation of Human Hepatitis A Virus in African Green Monkey Kidney Cell Culture: Primary and Serial Passage, *Infection and Immunity*, 32: 388–393. However, such methods are hereinafter referred to as "acute infection" procedures wherein multiple passages of cell free virus in tissue cultures are required before an acceptable virus titer is obtained. In accordance with acute infection procedures, a cell tissue culture is infected with a specimen containing hepatitis A virus. The infected cell culture is grown in an appropriate medium through "confluency" and then the fully grown cells are allowed to "age". The "aged" cells are "killed" and the virus is extracted. The extracted cell free virus is subsequently utilized to reinfect a new cell culture. This process is repeated several times, generally referred to as passages of the virus, until an acceptable virus titer is obtained. However, "acute infection" or so-called "reinfection" procedures are generally time consuming and inefficient in that such procedures generally involve termination of the infected cultures and infection of new cultures in order to obtain a suitable virus titer. As a result, material, manpower, and physical space requirements for tissue culture procedures utilizing acute infection techniques are high. Furthermore, some disclosed acute infection procedures are "indirect", that is, require repeated adaptation of the virus in marmosets before propagation in tissue cultures.

It is an object of the present invention to provide a tissue culture procedure for the production of hepatitis A virus in vitro, which eliminates the tedious and time consuming acute infection procedures requiring "reinfection" or repeated passages of cell free virus. Also, it is a further object of the present invention to provide a procedure for increasing the yields of hepatitis A virus obtained from a tissue culture procedure.

SUMMARY OF THE INVENTION

The present invention relates to a method for production of human hepatitis A virus in an in vitro cell culture system comprising maintaining a persistently infected virus producing cell line and harvesting hepatitis A virus from the persistently infected virus producing cell line. The present invention also relates to a method for establishing a persistently infected human hepatitis A virus producing cell line, said method comprising: (a) infecting a suitable cell culture with human hepatitis A virus and (b) maintaining the infected cell culture at log phase growth until the cell culture is capable of producing a stable virus titer. The present invention further relates to a method of increasing the yield of human hepatitis A virus obtained from an infected cell line, said method comprising harvesting the human hepatitis A virus from the infected cell line utilizing a nonphysiological mixture comprising a chelating agent and a nonionic detergent in a buffered medium.

The hepatitis A virus obtained as a result of the methods of the present invention is a source of viral antigens which are useful in diagnostic procedures for the detection of type A hepatitis.

DETAILED DESCRIPTION OF THE INVENTION

According to the present invention, hepatitis A virus is propagated in an in vitro cell culture system wherein said cell culture system comprises a persistently infected virus producing cell line. As used herein, the term "persistently infected virus producing cell line" refers to a virus infected cell line maintained at log phase growth and capable of producing a stable virus titer. To establish a persistently infected virus producing cell line, a suitable cell line is infected by means of a single treatment with an inoculum obtained from a human clinical specimen containing the virus, and the infected cell line is thereinafter maintained at log phase growth until essentially all the cells in the culture become infected and a stable virus titer is achieved. The term "maintained at log phase growth" refers to a process wherein infected cells of a culture are grown in a nutrient media until the cells reach confluency, generally within seven to ten days and thereafter upon reaching confluency and prior to "aging", the live infected cells are repeatedly subcultured, that is, a portion of the infected cell culture is transferred to a fresh culture vessel and again allowed to grow in a nutrient medium to confluency. The term, "stable virus titer", as used herein, refers to a cell culture system wherein essentially all of the cells in the culture are infected with the virus and each infected cell is producing large numbers of the virus. Generally, it has been found that a stable virus titer is obtained within four to five subcultures following the initial inoculation. Once a stable virus titer is achieved, that is, a persistently infected virus producing cell line is established, each succeeding subculture of the infected cell line thereafter becomes a persistently infected virus producing cell line capable of immediately producing a high virus titer. It should be noted that in the method of the present invention at no time prior to harvesting of the virus is it necessary that the infected cells be lysed, i.e., killed, and the resulting cell free virus utilized to reinfect a fresh culture, as required with acute infection techniques.

The term "suitable cell line" as used herein refers to a cell line capable of becoming persistently and stably infected, i.e., essentially every cell becomes infected, remains infected throughout its life cycle and transmits infection to its progency cells.

Illustrative of a "suitable cell line" effective in the method of the present invention include human liver tumor lines PLC/PRF/5 (hereinafter referred to as "Alexander") and Hep. G2 (hereinafter referred to as "G2") described in *Br. J. Cancer* (1976) 34, 509 and *Nature* (1979), Vol. 282, 615, respectively. It is preferred to employ the human liver tumor line "Alexander" in the methods of the present invention.

Subculturing of the infected cell culture is generally carried out utilizing conventional subculturing procedures, i.e., a trypsin procedure described in, for example, Earle W. R., *Tissue Culture*, Cowdry E. V. ed.

*Laboratory Technique in Biology and Medicine*, 2nd Ed. (1948).

The intracellar virus produced utilizing the persistently infected virus producing cell line of the present invention, may be harvested in accordance with known techniques employing conventional procedures and reagents to lyse and cells containing the virus. The preferred method for harvesting the hepatitis A virus is to first allow the infected cells of the persistently infected virus producing cell line upon reaching confluency to age for approximately two to ten days and preferably seven days. Following this "aging" period, the growth media is removed from the culture and the cells are lysed. The cell lysates are cleared of nuclei, cell organelles, and debris by centrifugation to yield hepatitis A virus. It has been found that the yields of virus are unexpectedly and significantly increased when the virus infected cells are lysed utilizing a nonphysiological solution comprising a chelating agent and a nonionic detergent in a buffered solution. The chelating agents and nonionic detergents employed in the methods of the present invention are readily ascertained by one of ordinary skill in the art and include for example, chelating agents such as sodium ethylenediaminetetracetate (EDTA) and nonionic detergents including, for example, polyethylene glycol p-isooctylphenyl ethers such as Triton X-100 (poly(oxy-1,2-ethanediyl),alpha-[4-(1,1,3,3-tetramethylbutyl)phenyl]-ω-hydroxy-(octoxynol 9)). The hepatatis A virus thus obtained possesses the necessary properties for the preparation of an antigen employed in diagnostic immunoassays.

The nutrient medium employed in the methods of the present invention is a medium sufficient to maintain the cells at temperatures permitting propagation of both the cells and the virus in the cell culture. Generally, such temperatures range from about 30° to 39° C. The nutrient growth medium may be, for example, Eagle's minimal essential medium, Delbecco's minimal essential medium RPM1-1640, Eagle's medium with HEPES buffer and L-15-a phosphate buffered medium. It is preferred to employ a phosphate or HEPES buffered medium. In addition, the growth media is generally supplemented with a mixture comprising from 10-30% fetal calf serum, 100 μg/ml of penicillin and 100 units of streptomycin. In addition, the pH of the persistently infected virus producing cell line is generally that of the medium employed, approximately a pH of 7.6. Furthermore, the buffered solution utilized to lyse the cells is generally at the same pH as the growth medium. It is preferred that the pH of the buffered solution be approximately 7.6.

The following illustrative, nonlimiting examples will serve to further demonstrate to those skilled in the art the present invention.

EXAMPLE I

Establishment of a Persistently Infected Virus Producing Cell Line

The hepatitis A virus inoculum employed in the examples was obtained from a human clinical fecal specimen that was clarified, filtered and diluted 1:10 (w/v) in phosphate-buffered saline. Prior to infection, an Alexander human liver tumor cell line was grown in a nutrient medium supplemented with 10% fetal calf serum, 100 μg/ml of penicillin and 100 units of streptomycin to mid-log phase (40-60% confluency) in 60 mm petri dishes. The cultures were then drained of the nutrient medium and treated with 2 ml of DEAE-dextran in unsupplemented media at 25 μg/ml at 37° C. for 20 minutes. To the DEAE-dextran treated cultures was added 4 ml of the filtered inoculum in complete medium at a 1:50 dilution. An uninfected control culture was similarly treated, except for infection with the inoculum. The medium was drained and replaced the next day. The infected and uninfected control cultures were subcultured approximately every seven days. The cultures were periodically monitored for evidence of hepatitis A virus replication by two types of immunoassays. Indirect immunofluorescence (IMF) assays were carried out on coverslip cultures using human immunoglobulins (IgG purified from a clinical sample of human serum) and fluorescein-conjugated goat antihuman IgG. This assay identified virus-producing cells by fluorescence-labeling. Utilizing the IMF techniques with respect to the infected cultures, fluorescent cells indicating infection, appeared as early as two to three weeks post-infection. At first, only 1%-2% cells in the cultures were fluorescent. On continued subculturing, a higher percentage of the cells were fluorescent, indicating increasing amounts of virus infected cells. The control cultures exhibited no fluorescence. Viral replication was also monitored by a solid-phase radioimmunoassay (RIA). The cells were lysed in phosphate buffered saline by repeated freezing and thawing. The cell extracts were clarified and then tested for viral antigen in an assay involving anti-HAV IgG-coated beads and $^{125}$I-labeled anti-HAV antibodies. The sensitivity and the results obtained as a result of the radioimmunoassay procedure were consistent with the results obtained from the IMF assays.

A persistently infected virus producing cell line was established within three months following infection; that is, the tissue cultures became essentially 100% infected and, thereafter upon subsequent subculturing, continuously produced high stable titers of hepatitis A virus.

Properties of the Persistently Infected Virus Producing Cell Line

The above-described persistently infected virus producing cell line was subcultured forty times over a period of eleven months. The following summarizes the characteristic properties of the persistently infected virus producing cell line thus established:

At subculture 2 (week 3), 2% of the cells become infected and were producing virus detectable by RIA and IMF assays. Following the sixth subculture, approximately week 7, 40-50% of the cells became infected. Following the ninth subculture and all subsequent subcultures, the virus producing cell line system had become positively infected. There was rapid horizontal spread of the virus ensuring the infection of every cell within the culture. Furthermore, on cell division, there must have been a consistent transmission of the virus to progency cells.

It has been noted that the established persistently infected virus producing cell line system did not require a special medium. Eagle's minimal essential medium, Delbecco's minimal essential, RPM1-1640, Eagle's medium with HEPES buffer and L-15 have been successfully employed. The cells of the virus-cell system have the same morphological and growth characteristics as the parent Alexander culture. The cells grow in monolayers under either stationary or dynamic conditions.

During the log-phase growth, cells of the persistently infected virus producing cell line system undergo cell division in about ten to sixteen hours. At a split ratio of 1:10, a subculture reaches confluency in seven to nine days, saturating at a cell density of $8 \times 10^4$ cells per cm$^2$. Confluent cultures could be held and allowed to age in a healthy state by changing to a maintenance medium containing 1% fetal calf serum instead of 10%. By changing with fresh maintenance medium every three days, it has been noted that the cultures could be held for more than two months.

To illustrate the hardiness of the parent cell line, infected Alexander cultures were left at room temperature without being fed fresh media for two weeks. The cells aged and many of the cells lysed and died while others exhibited severe pathological changes such as vacuolization, granulation, refractility, and long cytoplasmic processes. The cultures were fed maintenance medium and left unattended for more than two months. In spite of such neglect (harsh suboptimal conditions) these cells could be nurtured back to robust growth after several subculturing using proper care.

EXAMPLE II

Harvesting of the Virus

To harvest the virus, a subculture of the persistently infected virus producing cell line established in Example I is drained of nutrient media and washed with a solution of 1 mM EDTA in phosphate buffered saline. Following washing, the infected cells are detached and lysed simultaneously with a solution comprising 1 mM EDTA and 0.5% Triton X-100 in phosphate buffered saline. The lysed cells are incubated at room temperature for approximately 10-15 minutes. The cell lysates are centrifuged to clear nuclei, cell organelles and other debris to yield a clarified cell extract containing the hepatitis A virus.

Characterization of the Virus

The persistently infected virus producing cell system established in Example 1, replicates a virus having biophysical, morphological, immunological, and biological properties characteristic of hepatitis A virus isolated from human sources. The virus obtained as a result of the methods of the present invention banded with a bouyant density of CsCl of about 1.34 g/cc and a sedimentation velocity of about 160s in sucrose. The virus appeared as naked nucleocapsids, having a diameter of 27 nm, that can be specifically bound by human anti-hepatitis A virus antibodies in solid phase RIA. Upon inoculation onto fresh Alexander cells, the virus replicated to high titers. Upon inoculation into marmosets, the virus induced, within one week, clinical sysmptoms of hepatitis confirmable by serum glutamic pyruvic transaminase elevation and presence of hepatitis A virus antigens in fecal and liver extracts.

EXAMPLE III

The persistently infected virus producing cell line described herein readily adopted to mass virus propagation. In general, a large-scale scheme for producing hepatitis A virus utilizing a persistently infected virus producing cell line involves the maintenance of two lines of cultures: "stock": cultures and "production" cultures. Stock cultures provide infected cells to seed large numbers of production cultures which are intended for virus harvests, as well as a small number (1/10) of stock cultures for replenishment. Stock cultures are kept in the most vigorous state of growth. The stock cultures are seeded lightly ($5\times10^7$ cells per 6000 $cm^2$ cell factory) so that they reach confluency in approximately one week and are subcultured immediately. These cells are used to set up both stock cultures and production cultures. The cells are preferably subcultured at "late log phase", thereby permitting the cells to immediately divide without a lag period. It is important to examine the cultures microscopically on days one and two to confirm that the cells immediately divide. Seeding with aged, unhealthy, or damaged cells may result in a long lag period of three to seven days before the cells recover and divide, thereby delaying virus harvesting. Production cultures are seeded at a higher density ($10^8$ cells per cell factory) in order to allow the cultures to reach confluency earlier generally day five to seven. The production cultures are fed maintenance medium and upon reaching confluency are allowed to "age" for several days. Time course studies have indicated that the virus yield more than doubles during the "aging" period. The production cultures are sacrificed and harvested for virus generally between day ten to fourteen. A single stock culture generally provides in one week approximately enough cells for one stock and nine production cultures. Within one week, the nine production cultures yield on the average approximately $5\times10^8$ cells, $10^{12}$–$10^{13}$ infectious virus particles or $5\times10^8$ equivalent of antigen as measured using a standard radioimmunoassay procedure, employing Abbott's HAVAB RIA diagnostic kit and reagents.

The following describes a representative large-scale system:

Cell Culturing

An appropriate number of virus infected cells at late log phase growth and obtained from the persistently infected virus producing cell line established in Example 1 and are suspended in 1.8 l of complete medium (L-15 supplemented with 100 units per ml of penicillin, 100 μg/ml streptomycin and 10% fetal calf serum). The cell suspension is introduced by gravity flow into a cell factory (NUNC, 6000 $cm^2$) evenly distributing the cells among the ten layers. The seeding cell number for stock cultures is $5\times10^7$ and for production cultures, is $10^8$. The cell factory is kept at 37° C. and periodically microscopically examined to monitor cell growth.

Cell Subculturing

Stock cultures are subcultured utilizing a conventional trypsin procedure. The cell factory is drained of media, rinsed with 1 l of phosphate buffered saline and incubated with 0.8 l of 0.025% trypsin until cells lift. The cells are then collected. All operations are carried out by gravity flow at room temperature under sterile conditions. To the collected cells is added 40 ml of fetal calf serum and resulting cell suspension is centrifuged. The resulting cell pellet is gently resuspended in 50 ml complete medium. Cell yield is determined in a hemocytomer.

Virus Harvesting

Production cultures, upon reaching confluency generally on days five to seven, are drained of 90% of the medium and replaced with 90% fresh maintenance medium (same as previously employed except fetal calf serum is lowered to 2%). The cultures are incubated for an additional three to seven days. The cultures are drained, rinsed with 1.5 l of phosphate buffered saline and the cells are lysed with a mixture of 0.5 l phosphate buffered saline, 1 mM EDTA and 0.5% Triton X-100. The cell lysates are collected, and then clarified by centrifugation at 2000xg for ten minutes, and at 10,000xg for fifteen minutes at 4° C. The virus yield obtained is routinely measured by RIA.

EXAMPLE IV

Preparation of Hepatitis A Virus Antigen

Hepatitis A viral antigen is prepared by inactivating the tissue culture derived virus by conventional formalin treatment procedures. Generally, the virus extracted from the infected cells is incubated with a 1:4000 dilution of a 37% formaldehyde solution at 37° C. for three days and the resulting hepatitis A viral antigen is then collected.

As evidenced from the above Examples, the persistently infected hepatitis A virus producing cell line established in accordance with the methods of the present invention is effective in producing high titers of hepatitis A virus and hepatitis A viral antigen. It should be noted, that the number of subcultures necessary to establish a persistently infected virus producing cell line, following the initial inoculation of the cell line, is readily ascertained by one of ordinary skill in the art and will vary depending on factors such as, the source of inoculum, specific type of cell line and the like. In addition, other properties of the cell culture such as, for example, the number of cell divisions of the cell line is capable of, life-span of the cell line, rate of growth of the cell line, i.e., the time required for the cells to divide, number of subcultures that may be derived from the infected cell line, and the like, are readily ascertained, depending on the specific type of cell line initially infected in the procedures described above. Another advantage to the system described in the preceding Examples is the fact that carbon dioxide incubators are not required. In addition to the cell factory employed in Example 3, other suitable growth vessels, such as roller bottles have been successfully employed.

As previously mentioned, although other methods for lysing the virus from the infected cells may be employed, such as freeze-thawing techniques and physiological lysing solutions such as phosphate buffered saline, it is preferred to employ a nonphysiological solution comprising a chelating agent and a nonionic detergent in a buffered solution. It is preferred that phosphate buffered saline having a pH of about 7.6 be employed as the buffered solution. It has been found that the yields of hepatitis A viral antigen produced utilizing the chelating agent and the nonionic detergent to lyse the virus is approximately eight to nine times as great as the yields of hepatitis A viral antigen obtained utilizing lysing solutions that do not contain a nonionic detergent.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A tissue culture method for propagating hepatitis A virus in a hepatitis A virus-infected cell culture comprising the steps of:

(a) infecting a susceptible cell culture with a hepatitis A virus;
(b) growing the infected cells in the culture in a nutrient media until the cell culture reaches confluency;
(c) transferring some of the live, infected cells to a fresh nutrient media wherein the cells are maintained in log phase growth;
(d) repeating steps (b) and (c) until essentially all of the cells in the culture become infected and a persistently-infected hepatitis A virus-producing cell line is established; and,
(e) harvesting the hepatitis A virus.

2. A method according to claim 1 wherein the hepatitis A virus is harvested utilizing a nonphysiological mixture of a chelating agent and a nonionic detergent in a buffered solution to lyse the infected cells.

3. A method according to claim 2 wherein the nonphysiological mixture comprises sodium ethylenediaminetetraacetate and a polyethylene glycol p-isoctylphenyl ether in a buffered solution.

4. A method according to claim 3 wherein the polyethylene glycol p-isooctylphenyl ester is poly(oxy-1,2-ethanediyl),alpha-[4-(1,1,3,3-tetramethylbutyl)phenyl]-ω-hydroxy-(octoxynol 9).

5. A method according to claim 1 wherein the susceptible cell culture is infected by treating the cell culture with an inoculum obtained from a human clinical specimen containing hepatitis A virus.

6. A method according to claim 1 wherein the infected cell culture is obtained by treating a suitable cell culture with infected cells containing hepatitis A virus, wherein such infected cells are obtained from a persistently infected hepatitis A virus producing cell line.

7. A method according to claim 1 wherein the susceptible cell culture is an Alexander or G2 human liver tumor cell line.

8. A method according to claim 7 wherein the susceptible cell line is Alexander human liver tumor cell line.

9. A method according to claim 8 wherein the hepatitis A virus is harvested utilizing a nonphysiological mixture comprising a chelating agent and a nonionic detergent in a buffered solution to lyse the infected cells.

10. A method according to claim 9 wherein the nonphysiological mixture comprises sodium ethylenediaminetetraacetate and a polyethylene glycol p-isooctylphenylether in a buffered solution.

11. A method according to claim 1 wherein the cell culture, following step (a), reaches confluency within seven to ten days.

12. A method according to claim 1 wherein steps (b) and (c) are repeated from four to seven times before a persistently infected hepatitis A virus producing cell line is established.

13. A method according to claim 12 wherein steps (b) and (c) are repeated from four to five times before a stable persistently infected hepatitis A virus producing cell line is established.

14. A tissue culture method for establishing a persistently-infected hepatitis A virus-producing line, comprising the steps of:

(a) infecting a susceptible cell culture with a hepatitis A virus;
(b) maintaining the live, infected cells in the culture in a nutrient media until the cell culture reaches confluency;

(c) transferring some of the live, infected cells to fresh nutrient media wherein the cells are maintained in log phase growth; and, (d) repeating steps (b) and (c) until essentially all of the cells in the culture become infected and a persistently-infected hepatitis A virus-producing cell line is established.

15. A method according to claim 14 wherein the susceptible cell culture is infected by treating the cell culture with an inoculum obtained from a human clinical specimen containing hepatitis A virus.

16. A method according to claim 15 wherein the susceptible cell culture is an Alexander or G2 human liver tumor cell line.

17. A method according to claim 16 wherein the susceptible cell culture is Alexander human liver tumor cell line.

18. A method of growing hepatitis A virus in vitro comprising the steps of:

(a) growing cells infected with hepatitis A virus in a susceptible cell culture in a nutrient media at log phase growth;

(b) transferring some of the live, infected cells to fresh nutrient media wherein the cells are maintained at log phase growth; and, (c) repeating steps (a) and (b) until essentially all of the cells in the culture have become infected to produce a persistently-infected hepatitis A virus-producing cell line.

19. A method of growing hepatitis A virus in vitro comprising the steps of:

(a) growing cells infected with hepatitis A virus in a susceptible cell culture in a nutrient media at log phase growth;

(b) transferring some of the live, infected cells to fresh nutrient media wherein the cells are maintained at log phase growth;

(c) repeating steps (a) and (b) until essentially all of the cells in the culture have become infected to produce a persistently-infected hepatitis A virus-producing cell line; and (d) harvesting the hepatitis A virus.

* * * * *